United States Patent [19]
Neff

[11] Patent Number: 5,377,725
[45] Date of Patent: Jan. 3, 1995

[54] VISUAL MAGNIFICATION APPARATUS FOR A SYRINGE

[76] Inventor: Charles W. Neff, 953 Chartrand Ct., Ballwin, Mo. 63011-1515

[21] Appl. No.: 120,917

[22] Filed: Sep. 15, 1993

[51] Int. Cl.⁶ .......................................... B65B 3/00
[52] U.S. Cl. .................................... 141/27; 141/18; 141/95; 141/329; 141/375; 141/376; 141/383; 604/407; 604/414; 362/23; 362/109
[58] Field of Search ................. 604/407, 411, 414; 362/23, 109, 119, 120; 141/2, 18, 21, 25-28, 95, 319-321, 329, 330, 370, 372, 375, 376, 383; 222/39

[56] References Cited

U.S. PATENT DOCUMENTS

| | | | |
|---|---|---|---|
| 2,496,447 | 2/1950 | Dresser | 362/23 X |
| 2,827,558 | 3/1958 | Lents | 362/23 X |
| 3,844,318 | 10/1974 | Raia et al. | 141/27 |
| 4,252,159 | 2/1981 | Maki | 141/27 |
| 4,357,971 | 11/1982 | Friedman | 141/27 |
| 4,475,915 | 10/1984 | Sloane | 604/414 |
| 4,883,101 | 11/1989 | Strong | 141/27 |
| 5,247,972 | 9/1993 | Tetreault | 141/27 |
| 5,282,794 | 2/1994 | Propp | 604/411 X |

Primary Examiner—J. Casimer Jacyna

[57] ABSTRACT

A new and improved visual magnification apparatus for a syringe includes a base portion, a lens support portion attached to the base portion, and a magnifying lens attached to the lens support portion, wherein a syringe can be placed on the base portion and magnified by the magnifying lens. The base portion may include an internally concave cross-sectional contour that has a bottommost valley portion, such that a generally cylindrically-shaped syringe tends to rest in the valley portion under the influence of gravity. The base portion includes an ampule-supporting portion. The base portion also includes a slot portion capable of supporting a top portion of a syringe placed on the base portion. The base portion, the lens support portion, and the slot portion are in the form of a unified, integrated structure. The lens support portion may include an extension portion capable of retaining an ampule on the ampule-supporting portion of the base portion. An ampule alignment assembly may be connected to the base portion. An illumination assembly may be supported by the base portion. The location of the illumination assembly on the base portion is in opposition to the magnifying lens, such that the illumination assembly provides backlighting for the syringe when the syringe is positioned between the magnifying lens and the illumination assembly. An audible signalling assembly may be connected to either the base portion or to the lens support portion for providing an audible signal relating to syringe volume.

8 Claims, 4 Drawing Sheets

VISUAL MAGNIFICATION APPARATUS FOR A SYRINGE

BACKGROUND OF THE INVENTION

1. Field of the Invention

The present invention relates generally to hypodermic syringes, and more particularly, to an apparatus especially adapted for filling a hypodermic syringe to a desired level.

2. Description of the Prior Art

Devices designed to fill hypodermic syringes are well known in the art. For example, the following U.S. patents disclose some such known prior art syringe filling devices: U.S. Pat. Nos. 3,662,517; 4,489,766; 4,844,249; 4,940,460; and 4,998,570. More specifically, U.S. Pat. No. 3,662,517 discloses a syringe filling apparatus that is highly complex and expensive. In this respect, it would be desirable if a device were provided that aided filling a syringe that is not highly complex and expensive. Also, with this device, the apparatus itself mechanically fills the syringe. The person who intends to use the syringe does not actually fill the syringe. In this respect, it would be desirable if a device were provided that aided filling a syringe that permitted the user of the syringe to fill the syringe.

Many diabetics are visually impaired. Filling a syringe with the proper amount of insulin may be a difficult and dangerous task with assistance of a visually unimpaired person. However, a visually unimpaired person is not always available. Therefore, it is desirable that a visually impaired person be able to satisfactorily handle the task of filling a syringe with a proper amount of medication without the assistance of a visually unimpaired person.

U.S. Pat. No. 4,489,766 discloses a syringe filling device that is specifically designed to aid a blind or visually impaired person to fill a syringe. A plurality of retractable spacers of different thicknesses are located in a gauge portion to limit the extraction of the syringe plunger and thereby to control the quantity of medicine drawn into the syringe. The spacers are rearrangeable and removable to preselect the medicine dosage filling the syringe. One disadvantageous feature of this device is the need for someone of normal sight to arrange or rearrange the retractable spacers. A person of normal sight may not be needed if the retractable spacers have braille indicia and if a blind person knows braille. However, for a visually impaired person who does not know braille, use of this device would still require the assistance of a visually unimpaired person.

U.S. Pat. No. 4,844,249 discloses a medical supplies container that includes a number of supports for vials which receive specimens from a needle and syringe. There is no provision for proper filling of the syringes.

U.S. Pat. No. 4,940,460 discloses a patient-fillable and non-invasive hypodermic injection device assembly which includes a housing having an ampule-receiving chamber, a gas charge, and means for delivering a predetermined amount of gas to the ampule-receiving chamber. The complexities involved with a gas charge and means for delivering a predetermined amount of gas to the ampule-receiving chamber make this device unsuitable for use by a visually impaired patient. In this respect, it would be desirable if a device were provided that aided filling a syringe that is suitable for use by a visually impaired patient and that does not use a gas charge.

U.S. Pat. No. 4,998,570 discloses a filling device for a syringe that has an audible indicator which indicates and counts intake of dosage into the syringe. More specifically, a microprocessor controlled voice chip is used to give a voice readout of the syringe. A problem associated with this device is its complexity. Another problem is its bulk and size. It is not conducive to being portable and easily used away from a source of electric power. In this respect, it would be desirable if a device were provided that aided filling a syringe that is simple, not bulky, easily portable, and does not depend upon a source of electricity for operation.

Some persons who are visually impaired are able to see quite well when suitable optical magnification is provided to magnify that which is looked at. In this respect, it would be desirable if a device were provided that aided filling a syringe that employed visual magnification to magnify the syringe.

In filling a syringe from an ampule, it is important to align and stabilize the ampule with respect to the needle and the attached syringe. In this respect, it would be desirable if a device were provided that aided filling a syringe and that includes means for aligning and stabilizing the ampule with respect to the needle and the attached syringe.

When an object is magnified, often it is necessary to supply artificial illumination to the magnified object so that it can be more readily seen. Sometimes, it is desirable if the artificial illumination takes the form of backlighting, as opposed to light falling directly on the object being illuminated. Backlighting oftentimes provides the desirable characteristics of eliminating interfering reflected light such as glare. In this respect, it would be desirable if a device were provided that aided filling a syringe that provided magnification and artificial backlighting.

The benefits of audible signals for the visually impaired are well known. As discussed above, U.S. Pat. No. 4,998,570 provides complex, computer-generated, artificial voice signals to provide information with respect to syringe filling. Yet it would be desirable to be able to derive benefits of audible signals in filling a syringe without needing complex electronic computer-generated audible signals.

Very often visually impaired persons can take care of necessary syringe filling tasks by being able to form consistent habits with respect to their specific syringe filling needs. More specifically, a visually impaired person may consistently use syringes of a certain size. By doing so one may calibrate an audible signal with respect to the measured volume of the syringe that is filled. A series of audible signals may be calibrated to coincide with a corresponding series of syringe volumes. In this respect, it would be desirable if a device were provided that aided filling a syringe that provided a series of audible signals that correspond to a series of syringe volumes.

On the other hand, syringes, needles, and ampules come in a wide variety of sizes and cross-sectional contours. In this respect, it would be desirable if a device were provided that aided filling a syringe that is capable of handling a wide variety of sizes and shapes of syringes, needles, and ampules.

Thus, while the foregoing body of prior art indicates it to be well known to use aids for filling syringes, the prior art described above does not teach or suggest a visual magnification apparatus for a syringe which has the following combination of desirable features: (1) aids filling a syringe with apparatus that is not highly complex and expensive; (2) aids filling a syringe and permits the user of the syringe to fill the syringe; (3) aids filling a syringe by a visually impaired person that does not require the assistance of a visually unimpaired person; (4) aids filling a syringe that is suitable for use by a visually impaired patient and that does not use a gas charge; (5) is simple, not bulky, easily portable, and does not depend upon a source of electricity for operation; (6) aids filling a syringe that employs visual magnification to magnify the syringe; (7) aids filling a syringe and that includes means for aligning and stabilizing the ampule with respect to the needle and the attached syringe; (8) provides magnification and artificial backlighting for the syringe; (9) derives benefits of audible signals in filling a syringe without needing complex electronic computer-generated audible signals; (10) provides a series of audible signals that correspond to a series of syringe volumes; and (11) is capable of handling a wide variety of sizes and shapes of syringes, needles, and ampules. The foregoing desired characteristics are provided by the unique visual magnification apparatus for a syringe of the present invention as will be made apparent from the following description thereof. Other advantages of the present invention over the prior art also will be rendered evident.

SUMMARY OF THE INVENTION

To achieve the foregoing and other advantages, the present invention, briefly described, provides a new and improved visual magnification apparatus for a syringe which is comprised of a base portion, a lens support portion attached to the base portion, and a magnifying lens attached to the lens support portion, wherein a syringe can be placed on the base portion and magnified by the magnifying lens. The base portion may include an internally concave cross-sectional contour that has a bottommost valley portion, such that a generally cylindrically-shaped syringe tends to rest in the valley portion under the influence of gravity. The base portion includes an ampule-supporting portion. The base portion also includes a slot portion capable of supporting a top portion of a syringe placed on the base portion. The base portion, the lens support portion, and the slot portion are in the form of a unified, integrated structure. The lens support portion may include an extension portion capable of retaining an ampule on the ampule-supporting portion of the base portion.

An ampule alignment assembly may be connected to the base portion. The ampule alignment assembly is capable of receiving an upper portion of an ampule and of retaining the ampule in proper alignment with respect to a needle and a syringe attached to the needle.

An ampule securing assembly is provided for securing an ampule against the ampule alignment assembly. The ampule securing assembly may include an adjustable strap which includes a first strap end and a second strap end. The first strap end is attached to a portion of the base portion, and the second strap end is attached to a connector on the extension portion of the lens support portion. The second strap end of the adjustable strap may include a plurality of spaced adjustment apertures, such that a specific adjustment aperture can be selected for connecting the second strap end to the connector for securing a specific ampule to the base portion.

The ampule alignment assembly may include a rigid plastic substrate portion attached to the base portion, and a resilient upper portion covering the rigid plastic substrate portion. The resilient upper portion enables a close complementary fit between the upper portion of the ampule and the ampule alignment assembly.

An illumination assembly may be supported by the base portion. The location of the illumination assembly on the base portion is in opposition to the magnifying lens, such that the illumination assembly provides backlighting for the syringe when the syringe is positioned between the magnifying lens and the illumination assembly.

The illumination assembly includes a light source and a battery for powering the light source. A switch is connected between the light source and the battery for controlling power from the battery to the light source. The illumination assembly also includes a housing for housing the light source, the battery, and the switch.

An audible signalling assembly may be connected to either the base portion or to the lens support portion for providing an audible signal relating to syringe volume. The audible signalling assembly may include a signal element support member that is connected to either the base portion or to the lens support portion. A plurality of audible signal elements are sequentially spaced along the support member. The audible signal elements are positioned with respect to a syringe plunger handle, such that when the syringe plunger handle is moved with respect to a syringe barrel, the syringe plunger handle sequentially bumps up against a sequence of the audible signal elements, whereby the audible signal elements provide an audible signal relating to syringe volume.

An audible signal element may include an adhesive-coated bottom surface which permits selective placement of respective audible signal elements along the signal element support member.

The above brief description sets forth rather broadly the more important features of the present invention in order that the detailed description thereof that follows may be better understood, and in order that the present contributions to the art may be better appreciated. There are, of course, additional features of the invention that will be described hereinafter and which will be for the subject matter of the claims appended hereto.

In this respect, before explaining at least four preferred embodiments of the invention in detail, it is understood that the invention is not limited in its application to the details of the construction and to the arrangements of the components set forth in the following description or illustrated in the drawings. The invention is capable of other embodiments and of being practiced and carried out in various ways. Also, it is to be understood, that the phraseology and terminology employed herein are for the purpose of description and should not be regarded as limiting.

As such, those skilled in the art will appreciate that the conception, upon which disclosure is based, may readily be utilized as a basis for designing other structures, methods, and systems for carrying out the several purposes of the present invention. It is important, therefore, that the claims be regarded as including such equivalent constructions insofar as they do not depart from the spirit and scope of the present invention.

Further, the purpose of the foregoing Abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. Accordingly, the Abstract is neither intended to define the invention or the application, which only is measured by the claims, nor is it intended to be limiting as to the scope of the invention in any way.

It is therefore an object of the present invention to provide a new and improved visual magnification apparatus for a syringe which has all of the advantages of the prior art and none of the disadvantages.

It is another object of the present invention to provide a new and improved visual magnification apparatus for a syringe which may be easily and efficiently manufactured and marketed.

It is a further object of the present invention to provide a new and improved visual magnification apparatus for a syringe which is of durable and reliable construction.

An even further object of the present invention is to provide a new and improved visual magnification apparatus for a syringe which is susceptible of a low cost of manufacture with regard to both materials and labor, and which accordingly is then susceptible of low prices of sale to the consuming public, thereby making such visual magnification apparatus for a syringe available to the buying public.

Still yet a further object of the present invention is to provide a new and improved visual magnification apparatus for a syringe which aids filling a syringe with apparatus that is not highly complex and expensive.

Still another object of the present invention is to provide a new and improved visual magnification apparatus for a syringe that aids filling a syringe and permits the user of the syringe to fill the syringe.

Yet another object of the present invention is to provide a new and improved visual magnification apparatus for a syringe which aids filling a syringe for a visually impaired person that does not require the assistance of a visually unimpaired person.

Even another object of the present invention is to provide a new and improved visual magnification apparatus for a syringe that aids filling a syringe that is suitable for use by a visually impaired patient and that does not use a gas charge.

Still a further object of the present invention is to provide a new and improved visual magnification apparatus for a syringe which is simple, not bulky, easily portable, and does not depend upon a source of electricity for operation.

Yet another object of the present invention is to provide a new and improved visual magnification apparatus for a syringe that aids filling a syringe that employs visual magnification to magnify the syringe.

Still another object of the present invention is to provide a new and improved visual magnification apparatus for a syringe which aids filling a syringe and that includes means for aligning and stabilizing the ampule with respect to the needle and the attached syringe.

Yet another object of the present invention is to provide a new and improved visual magnification apparatus for a syringe that provides magnification and artificial backlighting of the syringe.

Still a further object of the present invention is to provide a new and improved visual magnification apparatus for a syringe that derives benefits of audible signals in filling a syringe without needing complex electronic computer-generated audible signals.

Yet another object of the present invention is to provide a new and improved visual magnification apparatus for a syringe which provides a series of audible signals that correspond to a series of syringe volumes.

Still a further object of the present invention is to provide a new and improved visual magnification apparatus for a syringe that is capable of handling a to wide variety of sizes and shapes of syringes, needles, and ampules.

These together with still other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there are illustrated preferred embodiments of the invention.

BRIEF DESCRIPTION OF THE DRAWINGS

The invention will be better understood and the above objects as well as objects other than those set forth above will become more apparent after a study of the following detailed description thereof. Such description makes reference to the annexed drawing wherein.

DESCRIPTION OF THE PREFERRED EMBODIMENT

With reference to the drawings, a new and improved visual magnification apparatus for a syringe embodying the principles and concepts of the present invention will be described.

Figure 1:
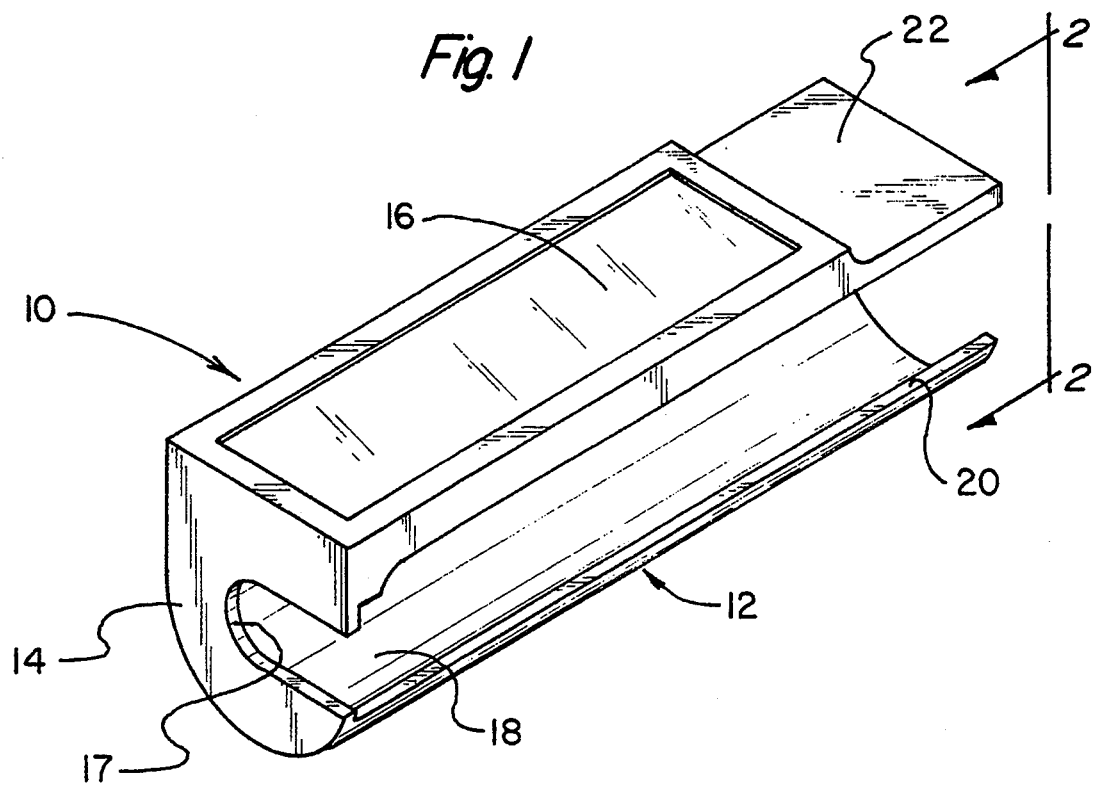
FIG. 1 is a perspective view showing a first preferred embodiment of the visual magnification apparatus for a syringe of the invention.
Figure 2:
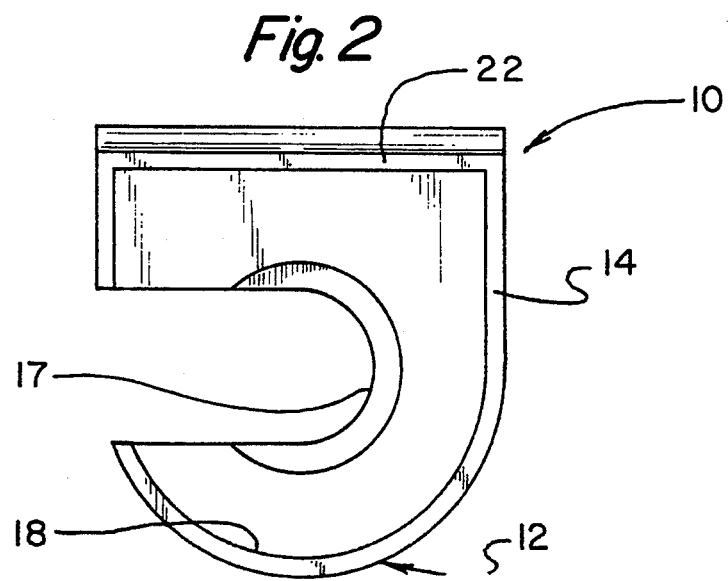
FIG. 2 is an enlarged end view of the embodiment of the invention shown in FIG. 1 looking down the end along line 2—2 of FIG. 1.

Turning initially to FIGS. 1-2, there is shown a first exemplary embodiment of the visual magnification apparatus for a syringe of the invention generally designated by reference numeral 10. In its preferred form, the visual magnification apparatus for a syringe 10 includes a base portion 12, a lens support portion 14 attached to the base portion 12, and a magnifying lens 16 attached to the lens support portion 14, wherein a syringe 11 can be placed on the base portion 12 and magnified by the magnifying lens 16. The base portion 12 includes an internally concave cross-sectional contour that has a bottommost valley portion 18, such that a generally cylindrically-shaped syringe 11 tends to rest in the valley portion 18 under the influence of gravity. When the syringe 11 rests in the valley portion 18 of the base portion 12, the syringe 11 is directly under the magnifying lens 16, and indicia on the syringe relating to the volume of syringe contents are readily magnified and seen by a user of the apparatus. The base portion 12 includes an ampule-supporting portion 20. The base portion 12 also includes a slot portion 17 in end wall 14 capable of supporting a top portion of a syringe 11 placed on the base portion 12. Alternatively, the base portion 12 may define an end wall 14 have a central circular opening in lieu of slot 17 with the circular opening being large enough for the syringe plunger to extend axially therethrough and being smaller enough to reatin the syringe barrel in an abutting manner interiorly of base portion 12.

The base portion 12, the lens support portion 14, and the slot portion 17 are in the form of a unified, integrated structure. The lens support portion 14 includes an extension portion 22 capable of retaining an ampule 13 on the ampule-supporting portion 20 of the base portion 12.

Figure 3:
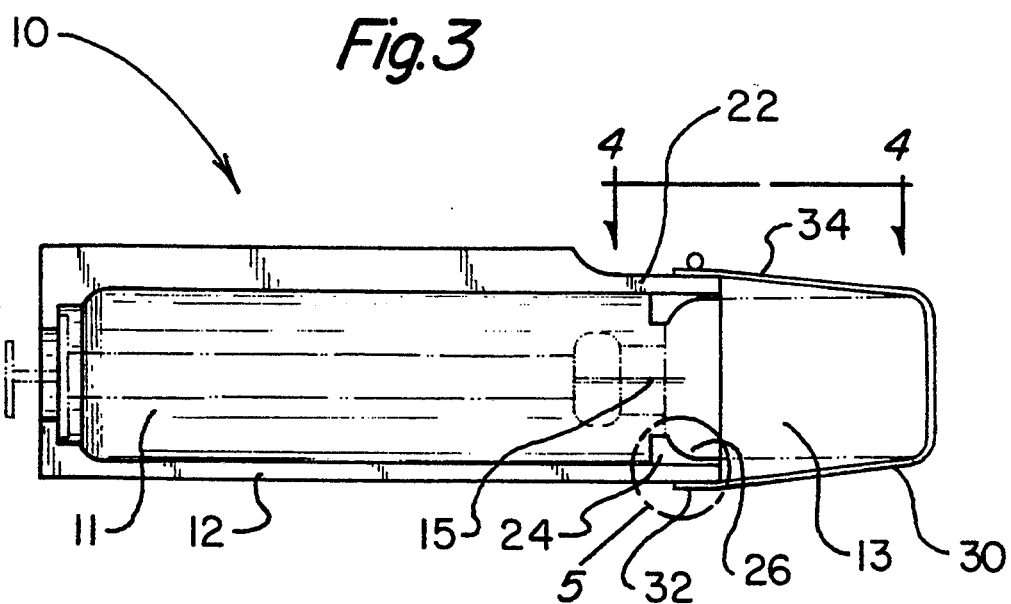
FIG. 3 is a cross-sectional side view of a second embodiment of the invention of a visual magnification apparatus for a syringe which includes an alignment assembly for aligning the ampule with the syringe.
Figure 4:
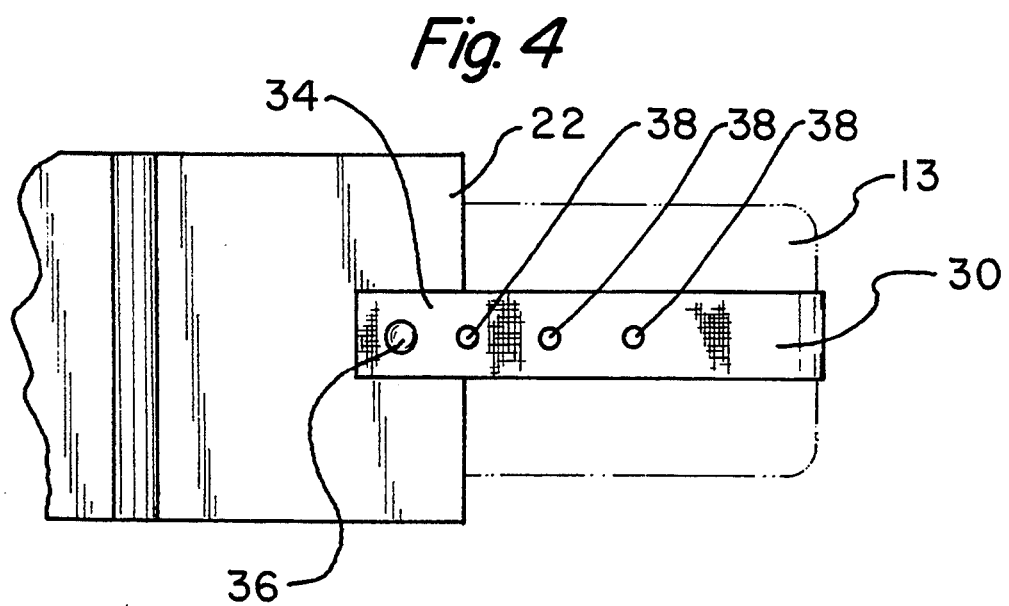
FIG. 4 is an enlarged, partial top view of the embodiment shown in FIG. 3 taken along the line 4—4 of FIG. 3.
Figure 5:
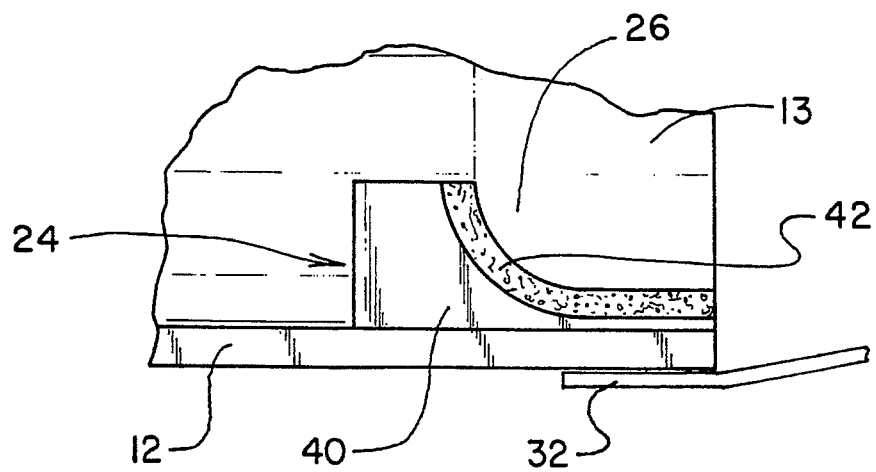
FIG. 5 is an enlarged partial cross-sectional view of the embodiment of the invention shown in FIG. 3 taken in the circled area 5 in FIG. 3.

Turning to FIGS. 3–5, a second embodiment of the invention is shown. Reference numerals are shown that correspond to like reference numerals that designate like elements shown in the other figures. In addition, an ampule alignment assembly 24 is connected to the base portion 12. The ampule alignment assembly 24 is capable of receiving an upper portion 26 of an ampule 13 and of retaining the ampule 13 in proper alignment with respect to a needle 15 and a syringe 11 attached to the needle 15.

Also as shown in FIGS. 3–4, an ampule securing assembly 28 is provided for securing an ampule 13 against the ampule alignment assembly 24. The ampule securing assembly 28 includes an adjustable strap 30 which includes a first strap end 32 and a second strap end 34. The first strap end 32 is attached to a portion of the base portion 12, and the second strap end 34 is attached to a connector 36 on the extension portion 22 of the lens support portion 14. The first strap end 32 can be connected to the base portion 12 by any suitable means such as an adhesive or a fastener such as a screw or rivet. The second strap end 34 of the adjustable strap 30 includes a plurality of spaced adjustment apertures 38, such that a specific adjustment aperture 38 can be selected for connecting the second strap end 34 to the connector 36 for securing a specific ampule 13 to the base portion 12. The adjustable strap 30 can be made of flexible, resilient material.

The ampule alignment assembly 24 includes a rigid plastic substrate portion attached to the base portion 12, and a resilient upper portion 42 covering the rigid plastic substrate portion 40. The resilient upper portion 42 enables a close complementary fit between the upper portion 26 of the ampule 13 and the ampule alignment assembly 24. The resilient upper portion 42 may be made from a resilient foam.

Figure 6:
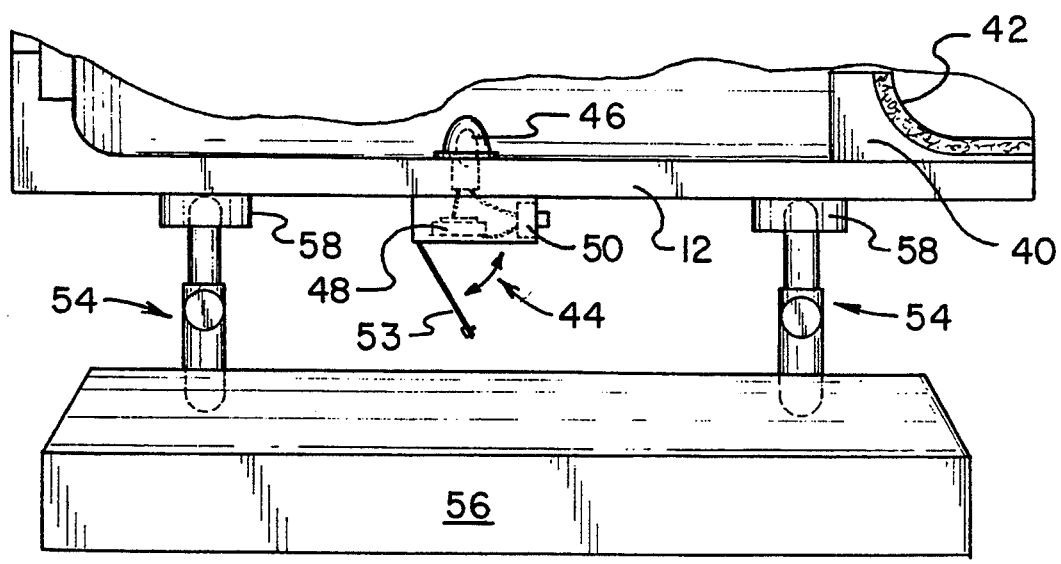
FIG. 6 is a partial cross-sectional view of a third embodiment of the visual magnification apparatus for a syringe of the invention in which a backlighting assembly is provided.

Turning to FIG. 6, a third embodiment of the invention is shown. Reference numerals are shown that correspond to like reference numerals that designate like elements shown in the other figures. In addition, an illumination assembly 44 is supported by the base portion 12. The location of the illumination assembly 44 on the base portion 12 is in opposition to the magnifying lens 16, such that the illumination assembly 44 provides backlighting for the syringe 11 when the syringe 11 is positioned between the magnifying lens 16 and the illumination assembly 44. Backlighting of the syringe 11 facilitates reading of syringe indicia as magnified by the magnifying lens 16.

The illumination assembly 44 includes a light source 46 and a battery 48 for powering the light source 46. A switch 50 is connected between the light source 46 and the battery 48 for controlling power from the battery 48 to the light source 46. The illumination assembly 44 also includes a housing 52 for housing the light source 46, the battery 48, and the switch 50. The housing 52 includes a door 53 that provides ready access to the interior of the housing 52 so that a spent battery or a spent light source can be readily replaced.

The base portion 12 may also be supported by telescopically adjustable legs 54 and a weighted base unit 56 which supports the adjustable legs 54. The adjustable legs 54 may fit into complementary fittings 58 on the bottom surface of the base portion 12.

Figure 7:
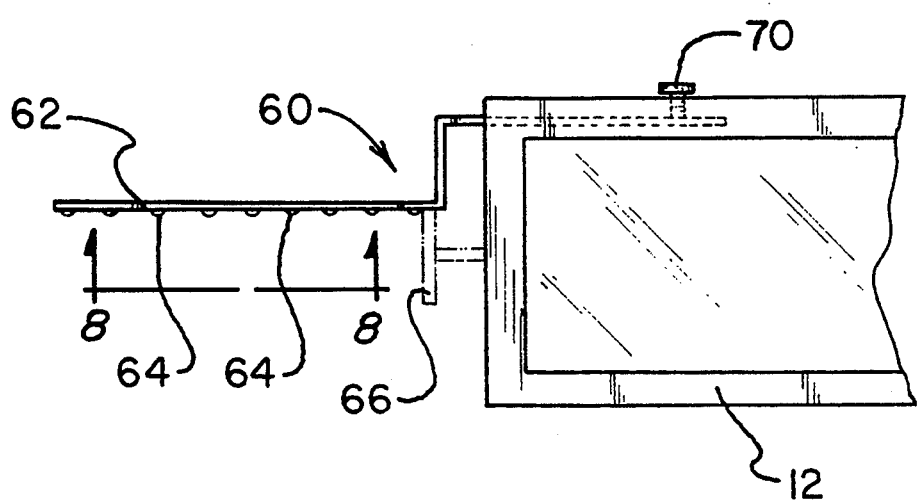
FIG. 7 is a partial side view of a fourth embodiment of the visual magnification apparatus for a syringe of the invention which includes an assembly for providing an audible signal of syringe volume.
Figure 8:
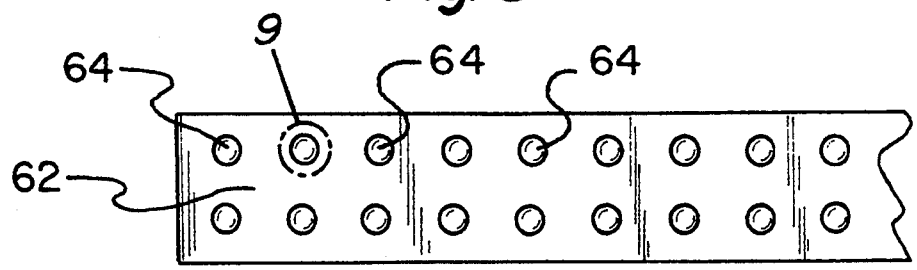
FIG. 8 is an enlarged, partial bottom view of the embodiment shown in FIG. 7 taken along the line 8—8 in FIG. 7.
Figure 9:
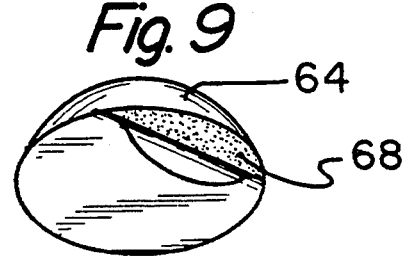
FIG. 9 in and enlarged, perspective view of an audible signaler shown in the circled area 9 in FIG. 8.

Turning to FIGS. 7–9, a fourth embodiment of the invention is shown. Reference numerals are shown that correspond to like reference numerals that designate like elements shown in the other figures. In addition, an audible signalling assembly 60 is connected to either the base portion 12 or to the lens support portion 14 for providing an audible signal relating to syringe volume. The audible signalling assembly 60 includes a signal element support member 62 that is connected to either the base portion 12 or to the lens support portion 14. A plurality of audible signal elements 64 are sequentially spaced along the support member 62. The audible signal elements 64 are positioned with respect to a syringe plunger handle 66, such that when the syringe plunger handle 66 is moved with respect to a syringe barrel, the syringe plunger handle 66 sequentially bumps up against a sequence of the audible signal elements 64, whereby the audible signal elements 64 provide an audible signal relating to syringe volume.

As shown in FIG. 9, an audible signal element 64 includes an adhesive-coated bottom surface 68 which permits selective placement of respective audible signal elements 64 along the signal element support member 62. If desired, the audible signal elements 64 can be placed along the signal element support member 62 at intervals corresponding to volume increments of the syringe 11. Alternatively, the audible signal elements 64 can be place along the signal element support member 62 at intervals corresponding to prescribed dosage intervals. A thumb screw 70 is employed to selectively attach the signal element support member 62 to or detach the signal element support member 62 from either the base portion 12 or the lens support portion 14.

The components of the visual magnification apparatus for a syringe of the invention can be made from inexpensive and durable metal, plastic, or glass materials.

As to the manner of usage and operation of the instant invention, the same is apparent from the above disclosure, and accordingly, no further discussion relative to the manner of usage and operation need be provided.

It is apparent from the above that the present invention accomplishes all of the objects set forth by providing a new and improved visual magnification apparatus for a syringe that is low in cost, relatively simple in design and operation, and which may advantageously be used to aid filling a syringe with apparatus that is not highly complex and expensive. With the invention, a visual magnification apparatus for a syringe is provided which aids filling a syringe and permits the user of the syringe to fill the syringe. With the invention, a visual magnification apparatus for a syringe is provided which aids filling a syringe for a visually impaired person without requiring the assistance of a visually unimpaired person. With the invention, a visual magnification apparatus for a syringe is provided which aids filling a syringe that is suitable for use by a visually impaired patient and that does not use a gas charge. With the invention, a visual magnification apparatus for a syringe is provided which is simple, not bulky, easily portable, and does not depend upon a source of electricity for operation. With the invention, a visual magnification apparatus for a syringe is provided which aids filling a syringe that employs visual magnification to magnify the syringe. With the invention, a visual magnification apparatus for a syringe is provided which aids filling a syringe and that includes means for aligning and stabilizing the ampule with respect to the needle and the attached syringe. With the invention, a visual magnification apparatus for a syringe is provided which provides magnification and artificial backlighting of the syringe. With the invention, a visual magnification apparatus for a syringe is provided which derives benefits of audible signals in filling a syringe without needing complex electronic computer-generated audible signals. With the invention, a visual magnification apparatus for a syringe is provided which provides a series of audible signals that correspond to a series of syringe volumes. With the invention, a visual magnification apparatus for a syringe is provided which is capable of handling a wide variety of sizes and shapes of syringes, needles, and ampules.

With respect to the above description, it should be realized that the optimum dimensional relationships for the parts of the invention, to include variations in size, form function and manner of operation, assembly and use, are deemed readily apparent and obvious to those skilled in the art, and therefore, all relationships equivalent to those illustrated in the drawings and described in the specification are intended to be encompassed only by the scope of appended claims.

While the present invention has been shown in the drawings and fully described above with particularity and detail in connection with what is presently deemed to be the most practical and preferred embodiments of the invention, it will be apparent to those of ordinary skill in the art that many modifications thereof may be made without departing from the principles and concepts set forth herein. Hence, the proper scope of the present invention should be determined only by the broadest interpretation of the appended claims so as to encompass all such modifications and equivalents.

What is claimed as being new and desired to be protected by LETTERS PATENT of the United States is as follows:

1. A new and improved visual magnification apparatus for a syringe, comprising:
    a base portion,
    a lens support portion attached to said base portion,
    a magnifying lens attached to said lens support portion, and
    an illumination assembly supported by said base portion, said illumination assembly located on said base portion in opposition to said magnifying lens, such that said illumination assembly provides backlighting for the syringe when the syringe is positioned between said magnifying lens and said illumination assembly, wherein said illumination assembly includes a light source, a battery for powering said light source, and a switch connected between said light source and said battery for controlling power from said battery to said light source, wherein said illumination assembly also includes a housing for housing said light source, said battery, and said switch, wherein said battery, said switch, and said housing are supported on a back side of said base portion such that said base portion is located between a syringe and said battery, said switch, and said illumination assembly housing,
    wherein a syringe can be placed on said base portion and magnified by said magnifying lens, wherein said base portion includes an internally concave cross-sectional contour having a bottommost valley portion, such that a generally cylindrically-shaped syringe tends to rest in said valley portion under the influence of gravity, wherein said base portion includes an ampule-supporting portion, wherein said base portion includes a slot portion capable of supporting a top portion of a syringe placed on said base portion.

2. The apparatus described in claim 1 wherein said base portion, said lens support portion, and said slot portion are in the form of a unified, integrated structure.

3. The apparatus described in claim 1 wherein said lens support portion includes an extension portion capable of retaining an ampule on said ampule-supporting portion of said base portion.

4. The apparatus described in claim 3 further including:
    an ampule alignment assembly connected to said base portion, said ampule alignment assembly capable of receiving an upper portion of an ampule and retaining the ampule in proper alignment with respect to a needle and a syringe attached to the needle.

5. The apparatus described in claim 4, further including:
    an ampule securing assembly for securing an ampule against said ampule alignment assembly.

6. The apparatus described in claim 5 wherein said ampule securing assembly includes:
    an adjustable strap which includes a first strap end and a second strap end, wherein said first strap end is attached to a portion of said base portion, and wherein said second strap end is attached to a connector on said extension portion of said lens support portion.

7. The apparatus described in claim 6 wherein said second strap end of said adjustable strap includes a plurality of spaced adjustment apertures, such that a specific adjustment aperture can be selected for connecting said second strap end to said connector for securing a specific ampule to said base portion.

8. The apparatus described in claim 4 wherein said ampule alignment assembly includes:
    a rigid plastic substrate portion attached to said base portion, and
    a resilient upper portion covering said rigid plastic substrate portion, said resilient upper portion enabling a close complementary fit between the upper portion of the ampule and the ampule alignment assembly.

* * * * *